United States Patent [19]

Brockway et al.

[11] Patent Number: 4,846,191

[45] Date of Patent: Jul. 11, 1989

[54] DEVICE FOR CHRONIC MEASUREMENT OF INTERNAL BODY PRESSURE

[75] Inventors: Brian P. Brockway, Minneapolis; Perry A. Mills, Roseville; Jonathan T. Miller, St. Paul, all of Minn.

[73] Assignee: Data Sciences, Inc., Roseville, Minn.

[21] Appl. No.: 199,697

[22] Filed: May 27, 1988

[51] Int. Cl.[4] ............................................. A61B 5/00
[52] U.S. Cl. .................................. 128/748; 128/673; 128/903
[58] Field of Search ............................... 128/672–675, 128/748, 903; 73/706–707

[56] References Cited

U.S. PATENT DOCUMENTS

| | | | |
|---|---|---|---|
| 3,550,583 | 12/1970 | Chiku . | |
| 3,893,451 | 7/1975 | Durand et al. . | |
| 3,958,558 | 5/1976 | Dunphy et al. . | |
| 4,160,448 | 7/1979 | Jackson | 128/673 |
| 4,325,387 | 4/1982 | Helfer | 128/748 |
| 4,385,636 | 5/1983 | Cosman | 128/748 |
| 4,407,296 | 10/1983 | Anderson | 128/675 |
| 4,483,196 | 11/1984 | Kurtz et al. | 73/730 |
| 4,485,813 | 12/1984 | Anderson et al. | 128/675 |
| 4,519,401 | 5/1985 | Ko et al. | 128/748 |
| 4,557,269 | 12/1985 | Reynolds et al. | 128/675 |
| 4,576,181 | 3/1986 | Wallace et al. | 128/675 |
| 4,610,256 | 9/1986 | Wallace | 128/675 |
| 4,741,345 | 5/1988 | Matthews | 128/748 X |

OTHER PUBLICATIONS

Meindl et al., "Implantable Telemetry in Biomedical Research"; *IEEE Trans. on Biomed. Engr.*; vol. BME-31, No. 12, 12-1984, pp. 817-823.

*Primary Examiner*—Kyle L. Howell
*Assistant Examiner*—Angela D. Sykes
*Attorney, Agent, or Firm*—Kinney & Lange

[57] ABSTRACT

Measurement of a physiological pressure is accomplished by placement of a pressure transmitting catheter within a blood vessel or other structure within which pressure is to be measured. The catheter is blood-compatible, capable of withstanding handling during distribution and implantation, and provides adequate pressure transmission frequency response in a variety of applications. The catheter, which includes a hollow flexible tube filled with a low viscosity fluid and having a plug of a gel-like material at its distal end, transmits the pressure signal to a solid-state transducer which is typically connected to amplifying electronics and an implantable radio-transmitter capable of relaying the pressure information from within the body to a radio receiver located external to the body.

42 Claims, 5 Drawing Sheets

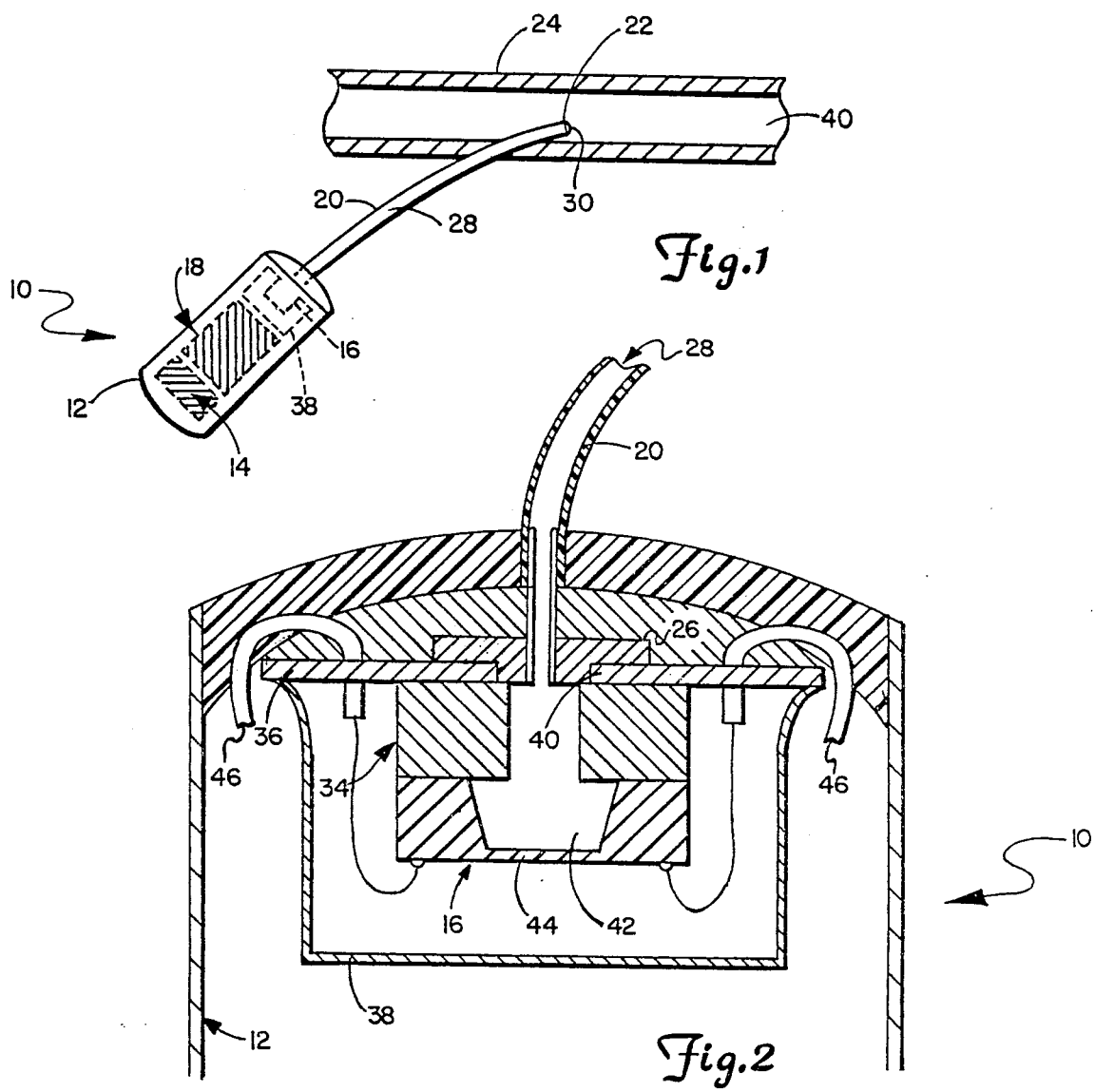
Fig.1
Fig.2
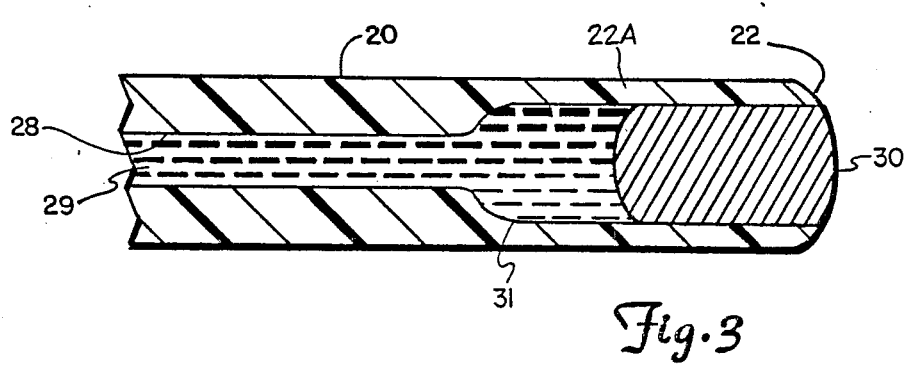
Fig.3

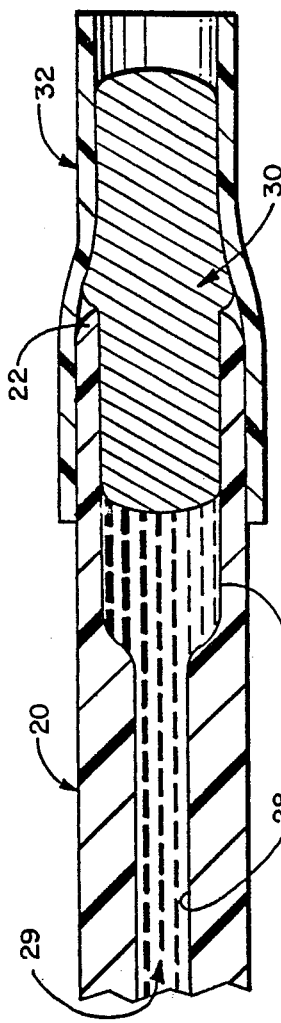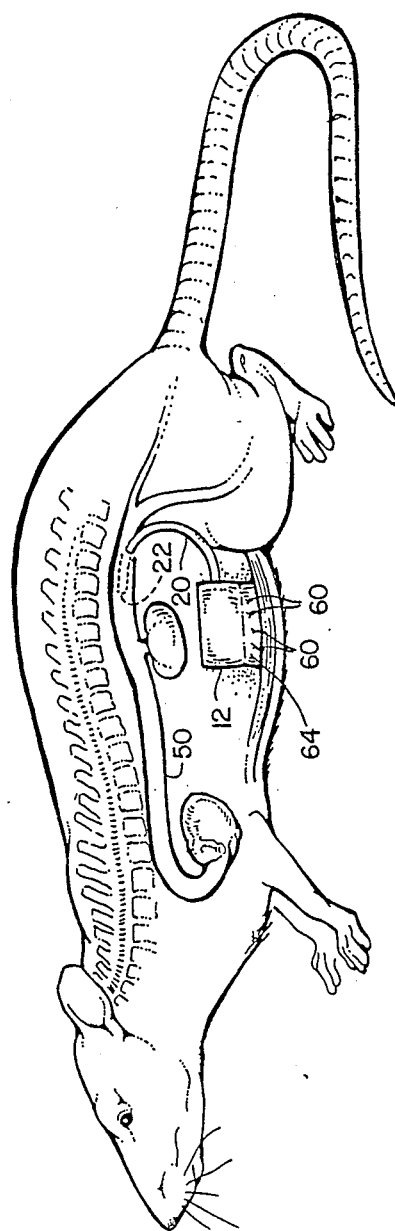
Fig. 4
Fig. 5

DEVICE FOR CHRONIC MEASUREMENT OF INTERNAL BODY PRESSURE

BACKGROUND OF THE INVENTION

1. Field of the Invention.

The present invention relates to a means of measuring physiological pressures, including blood pressure, intracranial pressure, intrapleural pressure (for evaluation of respiratory function and respiration rate), and pressure within the gastro-intestinal system. This invention is particularly useful for chronic measurement of pressures.

2. Description of the Prior Art

Measurement of physiological pressures is of interest to both clinicians and researchers. Such pressure measurements obtained from laboratory animals can provide researchers with valuable information with regard to the physiological response to pharmacological agents and toxicity of chemicals, and can lead to a better understanding of human physiology. The pressures which are most often of interest in animals are blood pressure, intrapleural pressure and intracranial pressure.

Blood pressure is of particular interest. Because blood pressure fluctuates over the course of time, it is often necessary to obtain chronic and frequently sampled measurements of blood pressure within a given animal in order to assess the affects of an agent over a time course. There are several methods which are currently used for chronic measurement of blood pressure. These include the tail cuff method, chronic cannulation, the use of implantable pressure sensors in combination with a telemetry backpack, and the use of vascular access ports.

The tail cuff method is well developed with several companies manufacturing devices which use this method. Some means is used to restrain the animal while an inflatable cuff is placed around the tail or leg. A blood flow sensor is typically integral to the cuff. The cuff is inflated until blood flow has ceased and is then deflated. The first indication of pulsatile flow is noted and recorded as the systolic pressure. These devices typically require that the arteries of the animal be dilated by heating the entire body of the animal to 40 degrees Celsius or more, causing significant stress on the animal and subsequent artifact. In addition, they are usually able to measure only systolic pressure. Since these devices require that the animal be restrained, artifact is introduced due to the stress of handling and restraint. In addition, it is not possible to humanely obtain measurements from an animal at frequent intervals with this method, and the method is very labor intensive.

Chronic cannulation is the most frequently used method for measurement of blood pressure for extended periods of time. With this method, a catheter is inserted into an artery. The catheter is exteriorized at a point (typically on the back of the neck) which generally prevents it from being destroyed by the animal. The catheters from a number of animals may be connected to a single pressure transducer through servo valves. A mechanical pump is typically used with each animal via a tether to continuously backflush the catheter with a heparinized saline solution. In addition, a swivel must be used on each catheter to prevent it from becoming tangled as the animal moves about the cage. The servo valves and pressure transducers are often connected to a computer to allow for frequent sampling of pressure. This method has several disadvantages. First, since the catheter is long and relatively small in diameter, the higher frequency components of the pressure waveform are often lost. Second, since the catheter is exteriorized, infections are common. Third, even though precautions are taken, the animals often become tangled in the catheter or learn to grab the catheter with their teeth or paws, and subsequently bleed to death. Fourth, keeping the catheters patent requires considerable maintenance and is thus labor intensive.

Implantable pressure sensors are sometimes used in combination with a telemetry transmitter placed in a backpack. This eliminates some of the disadvantages pointed out above. One manufacturer which supplies this type of equipment is Konigsburg Instruments (Pasadena, CA), which manufactures a number of sensors, the smallest of which is 3.5 mm in diameter. However, this sensor is too large for many applications, and since it is most frequently necessary to mount it in the wall of a vessel, it is subject to fibrous tissue growth over the sensing diaphragm which results in drift of the measured signal. In addition, the nature of the transducer is such that drift is inherent and requires frequent in-vivo calibration.

Miniature solid state sensors mounted on the tip of a catheter, such as those available from Millar Instruments (Houston, Tex.) and PPG Industries (Pleasantville, N.Y.), have also been used to measure internal body pressures. Some commercially available devices are as small as 1 mm diameter. Because of the inherent instability of these devices, they require calibration within a short time prior to use and are suitable only for acute measurements.

Another method involves implantation of a vascular access port in the animal. In this approach, a catheter is attached to a reservoir opposite a diaphragm. The catheter is placed in an artery, while the reservoir is placed under the skin to allow convenient access with a hypodermic needle. The reservoir can be accessed by piercing the skin and diaphragm with a needle. Connecting the needle to a pressure transducer allows for acquisition of pressure measurements and flushing of the catheter. The disadvantage of this approach is that it is labor intensive. A sterile protocol is required each time the diaphragm is pierced. In addition, the catheter requires bi-weekly flushing in order to maintain patentcy. If the sterile protocol is broken, the animal may develop infection, requiring expensive antibiotics and removal from the study until the infection clears. This is an expensive proposition considering that the company may have invested several thousand dollars in the animal at that point.

Intrapleural pressure is also of interest and can be used to determine the rate of respiration in addition to providing general information with regard to respiratory function. There are two methods which are commonly used to measure the rate of respiration in freely moving laboratory animals. Both methods have serious drawbacks.

One method is to use a small container which is tightly sealed, except for a controlled source of fresh air, and an exhaust port for discharge of stale air. As the animal breathes, small pressure flucuations occur within the container which can be detected by a pressure sensor. Variations in pressure can then be detected and provide a signal from which respiratory rate can be detected. This method is very accurate, but requires that the animal be placed in a cage which is often smaller than that allowed by government regulatory agencies. Therefore, it would be a violation of animal care rules to monitor respiration for more than a short time using this method.

Another method of determining respiratory rate in freely moving animals is to acquire blood pressure or electrocardiogram signals from freely moving animals and employ circuitry which can detect the modulation of these signals by respiration. The disadvantage of this method is that the modulation is often very weak or noisy. This method works relatively well on anesthetized animals, but changes in these signals caused by movement of awake animals often result in false indications.

Intracranial pressure is also of interest. Measurements of intracranial pressure from laboratory animals are often used to project which methods of treatment and management are most effective in human beings. Methods commonly used for monitoring intracranial pressure in animals include direct measurement via an exteriorized catheter or needle, or connection of a transducer to a port located on the skull of the animal. Devices such as those described by Ko (U.S. Pat. No. 4,519,401) have been used in only limited circumstances.

Chronic measurement of physiological pressures also provides vital information for clinical care of human beings. Patients with high blood pressure could benefit from an implantable device which could chronically monitor pressure as a means of determining optimal dosage for drug or bio-feedback therapy. Such a device could also be used as a means of providing feedback to a closed-loop drug delivery system for controlling blood pressure, or to a cardiac pacemaker as a means of optimizing pacing control parameters.

Infants who have been identified as being at risk for sudden infant death syndrome could also benefit. Currently, such infants are often monitored using a vest which detects changes in volume of the chest as breathing occurs. In certain instances, this method is not reliable. It would be desirable to monitor changes in intrapleural pressure as a reliable measurement of respiratory rate in these infants by a means which would allow the infant to roll and move freely about its crib without being restrained by wires extending from a vest.

Chronic monitoring of intracranial pressure is also important for infants with hydrocephalus and patients with head injury. Hydrocephalus and head injuries can cause excessive pressure build-up within the brain, resulting in death or serious brain damage. In most cases, corrective action can be taken if the build-up of pressure can be quickly detected. To detect such a build-up of pressure, a catheter is usually inserted into the brain through the skull and connected to a pressure sensor external to the patient. This offers the opportunity for infectious agents to enter along the catheter, often resulting in infections. In addition, catheters can become tangled when monitoring intracranial pressures in infants as they move about in their hospital crib. The present invention provides a means whereby chronic measurements of intracranial pressures could be obtained without the use of an exteriorized catheter.

SUMMARY OF THE INVENTION

The present invention is a device capable of sensing pressure in a manner which allows the sensor and amplifying electronics to be packaged in a very small size and implanted within the body. The sensor is attached to a flexible pressure transmission catheter (PTC), the distal tip of which is placed at the point where pressure is to be measured. The PTC contains a gel-like material at the distal tip which is capable of flowing as does a viscous fluid, and which contains intramolecular forces which make it very unlikely that any portion of this material will dissolve, break apart, sluff off or wash away when subjected to the fluid and mechanical forces present when measuring physiological pressures and when used in the context of this invention. This material provides a direct interface with the tissue or fluid of which the pressure is to be measured. The proximal portion of the catheter contains a low viscosity liquid which is insoluble in the gel-like material and which interfaces directly with the sensing element of the pressure transducer.

The present invention offers several advantages over the state-of-the art. This is the first device capable of accurately monitoring blood pressure chronically from conscious freely-moving animals without the use of a tether, or the need to infuse drugs to maintain patency of a catheter. This accuracy is accomplished by a design which allows for use of a stable, reliable, durable, and inexpensive solid-state sensing element, in combination with a means of transmitting pressure from the blood to the sensing element. This means of transmitting pressure from the blood to the sensing element is unique in that it is capable of transmitting this pressure with high fidelity for extended periods of time without maintenance. The ability to monitor conscious freely-moving animals is achieved by packaging the pressure sensor together with signal conditioning and wireless telemetry circuitry, and battery in a hermetically sealed housing constructed of biocompatible materials. The fully packaged device is implantable in animals as small as laboratory rats.

BRIEF DESCRIPTION OF THE DRAWINGS

FIG. 1 shows a preferred embodiment of the pressure sensing device of the present invention, partly in section, with the pressure transmission catheter (PTC) inserted in an artery of an animal.

FIG. 2 is a sectional view of a portion of the pressure sensing device of FIG. 1, including the proximal end of the catheter and the pressure transducer.

FIG. 3 is a sectional view of the distal end of the catheter.

FIG. 4 is a sectional view of the distal end of pressure transmission catheter showing a protective sleeve in place for transport and distribution.

FIG. 5 shows the pressure sensing device implanted in a laboratory rat, indicating the positioning of the body of the device, and location of the PTC within the vessel of the animal.

DETAILED DESCRIPTION OF THE PREFERRED EMBODIMENTS

1. The Pressure Measurement Device

Figure 6A:
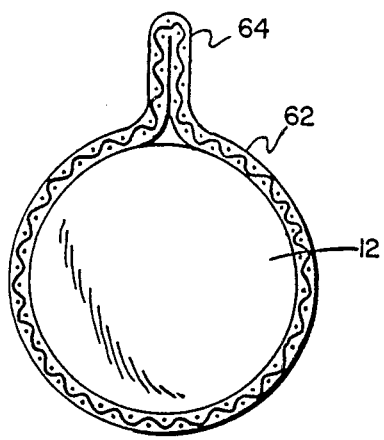
FIGS. 6A and 6B are end and perspective views of the body of the pressure sensing device and PTC showing a reinforced strap, provided as a means of securing the transmitter body in place.

Pressure measurement device 10 shown in FIGS. 1-4 is a very small, lightweight device which can be implanted into animals as small as rats, to provide chronic measurement of internal body pressures, such as blood pressure, intrapleural pressure or intracranial pressure. Device 10 includes housing 12 (which contains battery 14, pressure transducer 16, and signal processing-/telemetry circuitry 18), and pressure transmission catheter (PTC) 20. The distal tip 22 of pressure transmission catheter 20 is inserted into an artery 24 (or other entity within which pressure is to be measured) of an animal to transmit pressure of the fluid within artery 24 back to pressure transducer 16 within housing 12. The sensed pressure is converted to electrical signals by circuitry 18, and a telemetry signal is transmitted to a receiver external to the animal (not shown).

Catheter 20 is a small diameter, hollow tube which is mounted at its proximal end over nipple 26. Lumen 28 of catheter 20 is filled with low viscosity liquid 29 (see FIG. 3), which interfaces directly with pressure transducer 16. Fluid 29 is, in one preferred embodiment, an inert fluorinated hydrocarbon. Fluid 29 has a minimal biological activity (in case of failure of a seal), has a low thermal coefficient of expansion, is insoluble in gel 30, has a minimal rate of migration through the walls of catheter 20, and has a low viscosity at body temperature.

The distal end of catheter 20 has a thin-walled region 22A which defines an open cavity 31. A generally biocompatible and blood-compatible gel (or other gel-like material) 30 is contained in a distal portion of cavity 31 and provides a direct interface with the tissue or fluid of which the pressure is to be measured. Gel 30 provides a means of retaining fluid and is of a vicosity much higher than that of fluid 29. Gel 30 may be comprised of any material which is capable of flowing as does a viscous fluid and contains intramolecular forces which make it very unlikely that any portion of this material will dissolve, break apart, sluff off, or wash away when measuring physiological pressures and when using this device in the context of this invention. In a preferred embodiment of this invention, gel 30 is a silicone gel which contains cross-linked molecular entities.

Since the molecular entities of gel 30 are cross-linked, and since gel 30 has a tendency to adhere to the walls of cavity 31, gel 30 will not migrate out of cavity 31 or be washed away by body fluids or tissue impinging on distal tip 22, as would occur in a simple fluid-filled catheter. The ability of gel 30 to maintain its integrity is particularly key to monitoring blood pressure, where wash-out of material at the distal tip 22 of catheter 20 would result in the formation of fibrinous tissue within the lumen 28, leading to loss of fidelity of the pressure measurement. In addition, gel 30 is of a viscosity such that it can be displaced by small amounts within cavity 31 of catheter 20 without building up significant stresses which could result in a pressure differential across gel 30. The ability of gel 30 to be displaced by small amounts without developing a pressure differential allows device 10 to obtain accurate pressure measurements during changes in volume of catheter 20 due to bending and stress, and during thermal expansion and contraction of fluid 29. In one preferred embodiment, gel 30 is a hydrophobic material, which eliminates the possiblity of osmotic pressure across gel 30 or migration of blood solutes into gel 30. The length of gel 30 in cavity 31 of catheter 20 is typically about one (1) millimeter to about three (3) millimeters. A loosely or minimally crosslinked silicone-based gel is one example of a material which provides the necessary biocompatibility and adequate frequency response.

Catheter 20 is a biocompatible material with an outside diameter of about 0.5 to 1.5 millimeters and an inside diameter of about 0.3 to about 0.7 millimeters. The length of catheter 20 depends on the particular animal involved and is typically on the order of 5 to 6 centimeters for a rat and 15 to 25 centimeters for a dog. The inner diameter of cavity 31 of catheter 20 may be enlarged relative to the rest of catheter 20 in some applications, particularly when a very small catheter diameter is used. This reduces the distance the gel 30 will move during thermal expansion and contraction of that portion of fluid 29 located in pressure sensor well 42, and nipple 26. It also reduces movement of gel 30 due to changes in catheter internal volume induced by bending, thereby reducing artifact caused by flexing of catheter 20. In addition, the thin-walled portion 22A of catheter 20 provides for an improved dynamic response due to the ability of the thin wall to transmit rapid changes in pressure from the blood into fluid 29 contained within catheter 20. A catheter with an inner diameter of 0.35 mm, an outer diameter of 0.7 mm, a length of 6 cm, and gel 20 being 2 mm long has a dynamic response which is 3 decibels (db) down at about 30 Hz. By incorporating a 1 cm long thin-walled tip cavity with a wall thickness of 100 microns, all other dimensions being equal, the dynamic response improves to a 3 dB point of about 70 Hz.

Distal tip 22 of catheter 20 preferably is contoured to reduce trauma to the vessel and to inhibit turbulent flow when measuring blood pressure, as shown in FIGS. 1 and 3. In one embodiment, catheter 20 is fabricated of a urethane material, although other biocompatible materials may also be used.

In order to protect gel 30 during transport and distribution, protective tip cover 32 is applied (FIG. 4). During manufacture of the device, protective tip cover 32 is placed over distal tip 22 of PTC 20 prior to injecting gel 30. Gel 30 is then injected until it is at least 3 mm above the tip of catheter 20. Protective tip cover 32 filled with gel 30 in this manner allows PTC 20 to withstand extreme changes in temperature during sterilization and shipment by providing a reservoir of gel which can flow in and out of catheter 20 during thermal expansion and contraction. It also provides a reservoir of gel to offset expansion of the internal volume of catheter 20 during hydration of the catheter material prior to implantation. In one embodiment of this devise, protective tip cover 32 is fabricated of Silastic tubing.

In one preferred embodiment of the present invention illustrated in FIG. 2, transducer 16 is a solid state silicon piezoresistive bridge pressure sensor, which is mounted on a Pyrex pedestal 34, which in turn is mounted to a TO5 header 36 and which is enclosed and hermetically sealed so as to operate in a sealed-gauge mode within metal can 38 attached to TO5 header 36. TO5 header 36 contains a hole 40 centered on sensor cavity 42 to which nipple 26 is attached so as to form a pressure access port.

Transducer 16 has a cavity 42 which is in contact with and is filled by fluid 29, so that pressure is transmitted through gel 30 and through fluid 29 to diaphragm 44 of transducer 16. Electrical leads 46 connect transducer 16 to signal processing circuitry 18. Since transducer 16 operates as a sealed gauge unit, atmospheric pressure must be subtracted from the measured pressure to provide gauge pressure. Measurement of atmospheric pressure is obtained using an instrument designed for that purpose, with subtraction being performed by a computer system (not shown).

2. Preparation for Implantation of the Pressure Sensing Device

The implantation procedure used is, in general, dependent on the application. Regardless of the application, however, PTC 20 must be hydrated to allow it to expand to full volume and protective tip cover 32 must be removed. Hydration of PTC 20 involves soaking it in cool sterile physiologic saline for a minimum of 15 minutes. Soaking causes PTC 20 to absorb fluid and stabilize dimensionally prior to implantation. Exposing the device to cool saline causes the materials to contract. Warming to body temperature following implantation causes expansion of the fluid contents of PTC 20, forcing gel 30 slightly forward resulting in the formation of a "head" at the tip of PTC 20. This head provides an additional means which results in blood flowing smoothly past distal tip 22 of PTC 20 and eliminates voids in distal tip 22.

3. Use of the Device for Monitoring Blood Pressure in Laboratory Animals

In this application, the transmitter 10 is typically implanted in the peritoneal cavity or subcutaneously anterior to either the right or left flank.

a. Accessing Descending Aorta Via the Peritoneal Cavity

In this procedure (shown in FIG. 5), catheter 20 is introduced into the descending aorta 50 from within the peritoneal cavity and housing 12 remains within the peritoneal cavity upon completion. The procedure for implantation of the device in the peritoneal cavity of a rat involves anesthetizing the animal, performing a laparatomy at the abdominal midline, and exposing descending aorta 50 posterior to the renal cavity. A vessel clamp is applied to the descending aorta 50 immediately posterior to the renal artery to inhibit the flow of blood during introduction of the distal end 22 of catheter 20 into aorta 50. Catheter 20 is inserted first by puncturing a hole in aorta 50 with a hypodermic needle which is curved such that the beveled portion of the needle is on the outside of a radius. The end of the needle is inserted approximately 1-2 mm into aorta 50. While maintaining the hypodermic needle in position, catheter 20 is grasped with a small forceps immediately proximal to cavity 31. Catheter 20 is then delicately inserted into aorta 50 by sliding it next to the beveled portion of the needle. Once catheter 20 has entered aorta 50, the needle is retracted and catheter 20 is further inserted until all of thin-walled portion 22A of catheter 20 (i.e. cavity 31) resides within aorta 50. A loosely woven non-absorbable fabric (not shown) is then placed over the point of entry of catheter 10 into aorta 50. Tissue adhesive is then applied to the point where catheter 20 enters aorta 50 such that it contacts catheter 20 and the fabric so as to cause them to adhere to each other. A few days following surgery, the fabric becomes attached to surrounding tissue via fibrotic growth, resulting in chronic stabilization of catheter 20 at the point where it enters aorta 50. The vessel clamp is then removed and the contents of the peritoneum are returned to their original position. Housing 12 is secured to the abdominal musculature via sutures 60 which pass through the muscle wall at the incision, through flap 64 of reinforced Silastic strap 62 and through the musculature on the opposite side of the incision. The procedure is completed by closing the remainder of the incision and the skin.

Figure 6B:
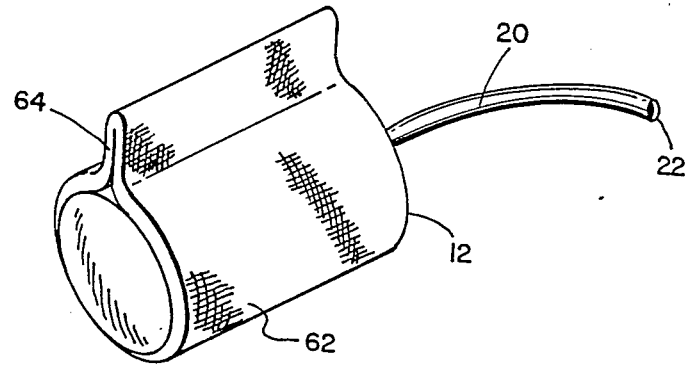

FIGS. 6A and 6B show strap 62 in further detail. Strap 62 surrounds housing 12 and has a folded flap 64 to which sutures 60 may be attached.

b. Accessing Descending Aorta Via the Femoral Artery

This approach provides an advantage over a peritoneal implant since it offers the opportunity for subcutaneous implantation. The subcutaneous implant approach offers the advantage of a shorter recovery period following surgery because it is a less invasive procedure. In this procedure, the catheter enters the femoral artery at either of the rear legs and is inserted until positioned in the descending aorta. This procedure is performed under anesthesia and begins by making an incision at the groin. The femoral artery is dissected and ligated posterior to the desired point of entry. Using a curved 20-gauge needle in the same manner as for insertion in the descending aorta, catheter 20 is inserted into the femoral artery until the entire thin-walled portion resides in the descending aorta. A pocket is formed under the skin anterior to the incision using a blunt-end scissors. Housing 12 is inserted into the pocket and is secured to the surrounding tissue with silk sutures 60 through flap 64. The incision is then closed with either wound clips or silk sutures and catheter 20 is secured at the point of entry to the femoral artery with tissue adhesive.

Although the procedures outlined here have proven successful for the measurement of blood pressure, other methods utilizing alternate placement of the device and methods for insertion of the catheter are possible.

4. Use of the Device for Monitoring Intrapleural Pressure

The respiratory rate of laboratory animals is an important parameter to measure in the study of respiratory physiology and the effect of drugs on the respiratory system. It can also provide an effective means of determining respiration in infants which are at risk of sudden infant death syndrome.

Pressure of the pleural cavity varies during a normal respiratory cycle, dropping to a negative value during inspiration, and rising during expiration. Respiratory rate can be determined by measuring the period of this cycle of rising and falling pressure. Device 10 of the present invention can be used to measure respiratory rate by inserting distil tip 22 of catheter 20 into the pleural space.

The details of the procedure outlined below are focused specifically on monitoring respiratory rate in a laboratory rat. However, the basic principles and techniques outlined here could be applied equally well to other species and to human beings.

Figure 7:
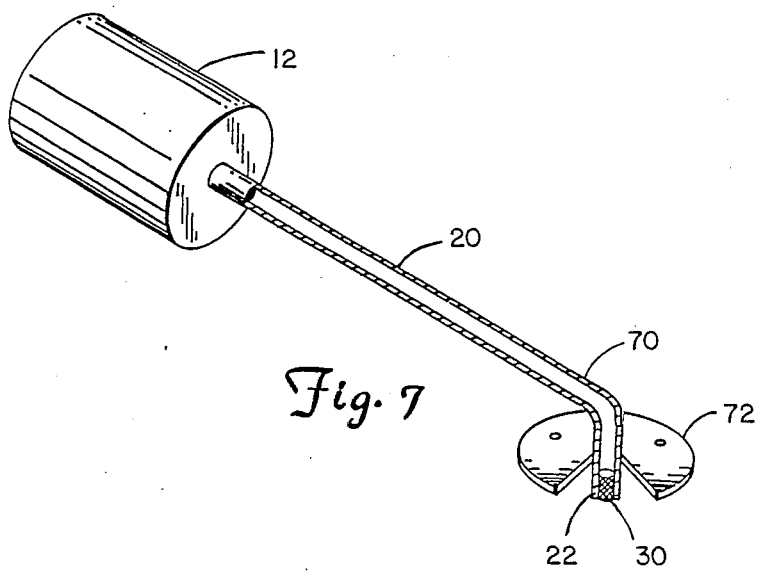
FIG. 7 shows (in a partial sectional and broken away view) the pressure sensing device with the distal end of the PTC modified to accomodate the requirements of measuring intracranial pressure and intrapleural pressure.

As shown in FIG. 7, pressure transmission catheter 20 is slightly modified from that used to measure blood pressure. In the design for monitoring intrathoracic pressure, the thin-walled portion of the PTC tip (i.e. cavity 31) is much shorter, elbow 70 is incorporated to orient distal tip 22 at a right angle to the main portion of catheter 20, and a plate or flange 72 is positioned by elbow 70 to provide a means of securing tip 22 of PTC 20 in the thorax. The distance from plate 72 to distal tip 22 is chosen to allow the entire cavity 31 of PTC 20 to extend into the thorax. The length of cavity 31 can be significantly reduced in this application with no adverse effects, since the required frequency response is much less than is needed for blood pressure.

The implantation procedure involves placing housing 12 under the skin of the abdomen, tunneling the pressure transmission catheter 20 under the skin to an appropriate site on the chest, and inserting the distal tip 22 of the pressure transmission catheter (PTC) 20 into the pleural cavity via an intercostal space. In the example below, PTC 20 enters via the ninth intercostal space near the sternum.

Figure 8A:
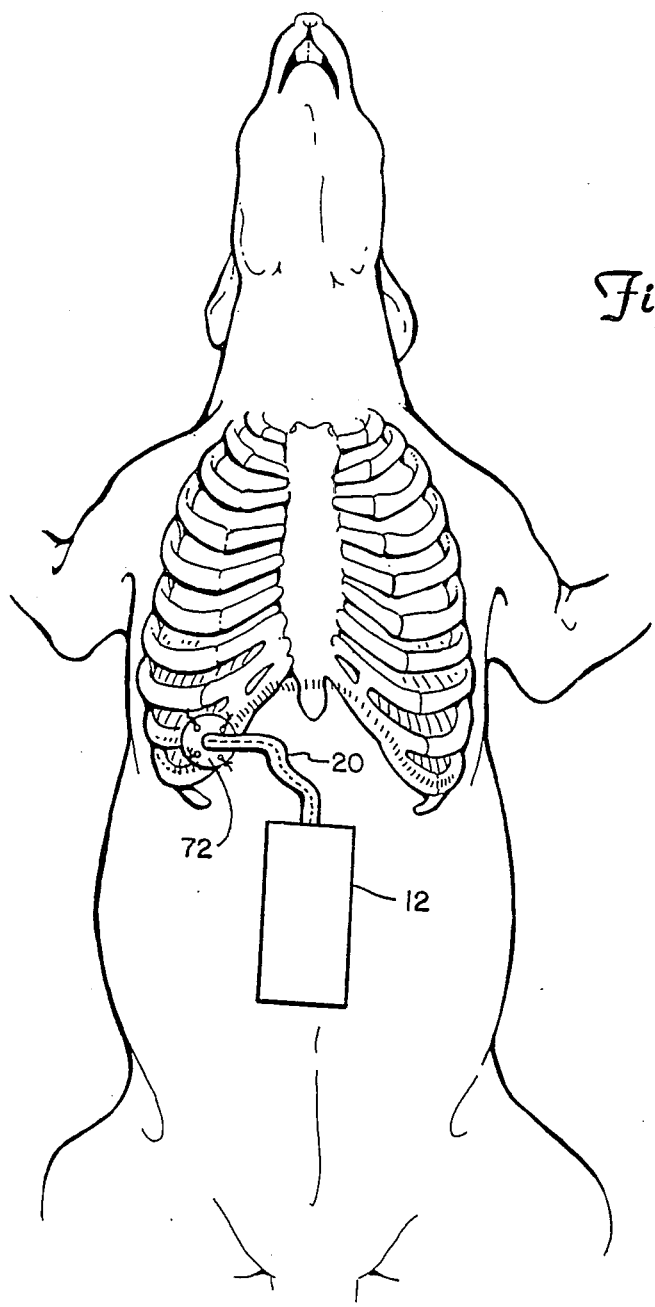
FIGS. 8A and 8B show ventral and lateral views of the pressure sensing device implanted in a laboratory rat for the purpose of measuring intrapleural pressure.
Figure 8B:
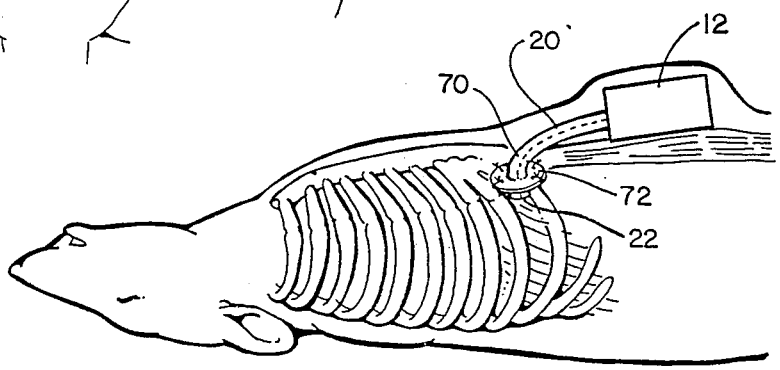

The procedure (illustrated in FIGS. 8A and 8B) begins by making a lateral incision 1 cm anterior to the desired location of housing 12. A pouch is then formed under the skin posterior to the incision by blunt dissection and housing 12 is inserted into this pouch. A second incision is made on the thorax near the sternum at the ninth intercostal space. PTC 20 is threaded under the skin to extend out of the thoracic incision. The musculature exposed at the thoracic incision is punctured at the ninth intercostal space with a blunt instrument having a diameter approximately 25% larger than that of the most distal point of PTC 20. The protective cover 32 on PTC 20 is then removed and PTC 20 is inserted into the pleural space until plate 72 is flush with the thoracic wall. Elbow 70, in conjunction with plate 72, serves to secure catheter distal tip 22 in a fixed position on the thoracic wall. In addition, elbow 70 serves to define and maintain the shape of PTC 20 as it turns 90° to enter the pleural space. The implant procedure is completed by securing housing 12 in place with sutures which pass through the reinforced Silastic strap 62 into the abdominal musculature, securing PTC tip 22 by suturing through plate 72 into the thoracic musculature, and then closing the incisions with wound clips.

5. Use of the Device for Monitoring Intracranial Pressure

Intracranial pressure is an important parameter to measure in laboratory animals for research purposes. In addition, it is often necessary to measure this parameter in humans who have been subjected to head injury or a disease such as hydrocephalus. These maladies can cause increases in intracranial pressure which can result in permanent brain damage. Measurement of intracranial pressure allows preventive action to be taken prior to extended exposure of the brain to pressures which can cause such damage.

The details of the procedure outlined below are focused specifically on monitoring intracranial pressure in a laboratory rat. However, the basic principles and techniques outlined here could be applied equally well to other species and to human beings. The design of PTC 20 for monitoring intracranial pressure is identical to that required for monitoring intrathoracic pressure, with the exception of the length of the thin-walled portion of catheter 20. In this application, this length is chosen so that distal tip 22 of catheter 20 protrudes past the inner lining of the skull about 0.1 to 0.5 millimeters. The pressure measured is therefore that of the subarachnoid cavity.

Figure 9:
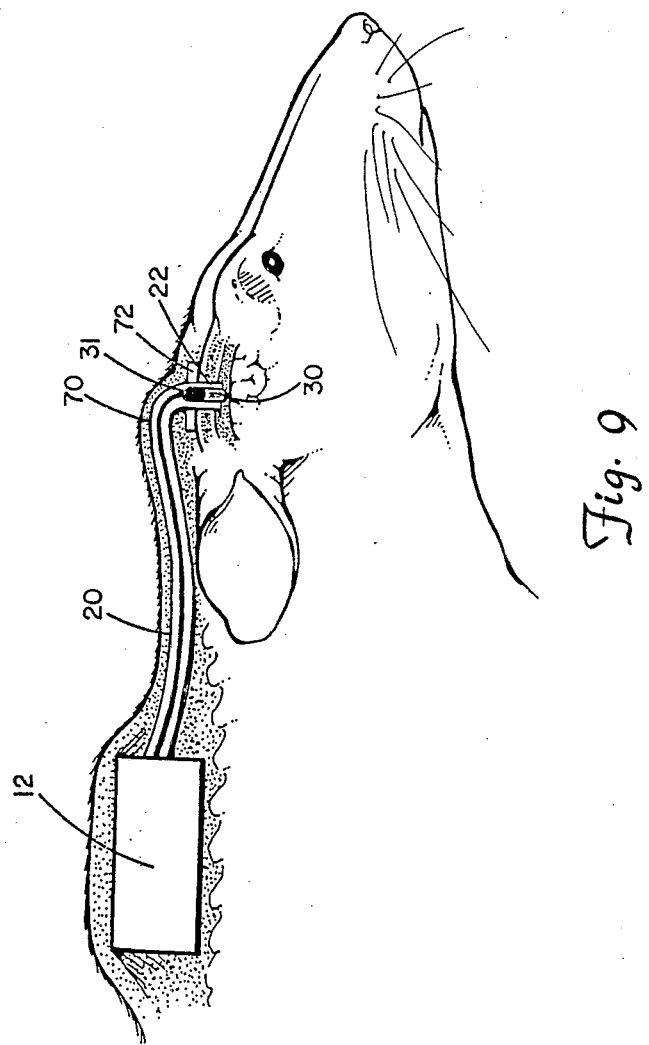
FIG. 9 provides a lateral view of the pressure sensing device implanted in a laboratory rat for the purpose of measuring intracranial pressure.

The implantation procedure (illustrated in FIG. 9) involves placing housing 12 under the skin above the scapulae, tunneling PTC 20 under the skin to the desired site on the cranium, inserting tip 22 of PTC 20 through through a hole drilled in the skull, and securing tip 22 of PTC 20 and housing 12. In the example below, PTC 20 enters the cranium above the parietal lobe.

The procedure begins by making a lateral incision 1 cm posterior to a line drawn between the ears. A pouch is then formed under the skin posterior to the incision by blunt dissection. A second incision is made on the skull above the parietal lobe. Housing 12 is placed in the subcutaneous pouch and PTC 20 is threaded under the skin to extend out of the incision located on the skull. A hole is then drilled through the skull large enough to allow free passage of PTC 20 through the skull bone. Protective cover 32 on PTC 20 is then removed and PTC 20 is inserted into the hole until plate 72 is flush with the skull. As in the case of the design for measuring intrathoracic pressure, elbow 70 in conjucntion with plate 72, serves to secure distal tip 22 in a fixed position. In addition, elbow 70 serves to define and maintain the shape of PTC 20 as it turns 90°. The implant procedure is completed by securing housing 12 in place with sutures which pass through flap 64 into the musculature, securing tip 22 of PTC 20 by suturing through the plate into the musculature, and closing the incisions with wound clips.

6. Conclusion

The device of the present invention overcomes serious disadvantages of the prior art and offers significant new opportunities in the chronic measurement of pressure. With the present invention, combined with a radio telemetry system and computerized data collection system, there is the capability of automating the process of collection of data from laboratory animals, and therefore providing better quality and more frequent data while generally reducing the cost of implementing the experimental protocol. With the present invention, in which the device is totally implanted, the animals are allowed to move freely within their cages, not only reducing stress caused by tethers but also providing for more humane treatment of the animals.

The device of the present invention is also applicable to sensing of internal body pressures in humans, including blood pressure, intrapleural pressure, intracranial pressure, and pressures within the gastro-intestinal system. Chronic pressure information sensed with the present invention is then available for diagnostic purposes or feedback for closed loop control of infusion pumps capable of administering pharmaceutical agents. This device offers the advantage that accurate measurements can be obtained without the need for exteriorized wires or catheters.

Although the present invention has been described with reference to preferred embodiments, workers skilled in the art will recognize that changes may be made in form and detail without departing from the spirit and scope of the invention.

What is claimed is:

1. A pressure measurement device for measuring a physiological pressure, the device comprising:
pressure transducer means for providing a signal which varies as a function of pressure;
pressure transmitting catheter means for transmitting the physiological pressure to the pressure transducer means, the pressure transmitting catheter means including a hollow flexible tube having a first end for placement at a position at which the physiological pressure is to be measured, a second end in communication with the pressure transducer means, a gel-like material positioned in the tube at the first end, and a liquid which fills the tube and interfaces with the pressure transducer means for transmitting pressure from the gel-like material to the pressure transducer means.

2. The pressure measurement device of claim 1 wherein the liquid is a hydrophobic liquid.

3. The pressure measurement device of claim 2 wherein the hydrophobic liquid is an inert fluorinated hydrocarbon.

4. The pressure measurement device of claim 1 wherein the liquid is substantially insoluble in the gel-like material.

5. The pressure measurement device of claim 1 wherein the liquid has a lower viscosity than the gel-like material.

6. The pressure measurement device of claim 1 wherein the tube is formed by a polymeric material.

7. The pressure measurement device of claim 1 wherein the tube is a urethane material.

8. The pressure measurement device of claim 1 wherein the gel-like material is a hydrophobic gel.

9. The pressure measurement device of claim 1 wherein the gel-like material is a silicon-based material.

10. The pressure measurement device of claim 1 wherein the gel-like material has a length of between about 1 millimeter and about 3 millimeters.

11. The pressure measurment device of claim 1 wherein the tube has an outside diameter of between about 0.5 millimeter and about 1.5 millimeters.

12. The pressure measurement device of claim 11 wherein the tube has an inside diameter of between about 0.3 millimeter and about 0.7 millimeters.

13. The pressure measurement device of claim 1 wherein the first end of the tube has a contoured tip.

14. The pressure measurement device of claim 1 and further comprising housing means for containing the pressure transducer means.

15. The pressure measurement device of claim 14 and further comprising:
signal processing and telemetry circuitry located in the housing means and electrically connected to the pressure transducer means for providing telemetry signals based upon the signal which varies as a function of pressure.

16. The pressure measurement device of claim 14 and further comprising a strap surrounding the housing means and having a flap to which sutures may be connected.

17. The pressure measurement device of claim 1 wherein the tube has a cavity at its first end in which the gel-like material is positioned and which contains the liquid.

18. The pressure measurement device of claim 17 wherein a portion of the tube containing the cavity has a smaller wall thickness then other portions of the tube.

19. The pressure measurement device of claim 1 and further comprising a mounting plate through which the first end of the tube extends.

20. The pressure measurement device of claim 19 wherein the tube has an elbow proximate the mounting plate.

21. The pressure measurement device of claim 1 and further comprising:
a protective sleeve at least partially filled with gel-like material mounted on the first end of the tube and removable during implantation of the tube into a body of an animal.

22. A pressure measurement device for measuring a physiological pressure, the device comprising
pressure transducer means for providing a signal which varies as a function of pressure;
pressure transmitting catheter means for transmitting the physiological pressure to the pressure transducer means, the pressure transmitting catheter means including a hollow flexible tube having a distal end for placement at a position at which the physiological pressure is to be measured, a proximal end in communication with the pressure transducer means, a lumen extending from the proximal to the distal end, a cavity in the distal end in communication with the lumen, a plug positioned in the cavity, and a liquid which fills the lumen and a portion of the cavity and interfaces with the pressure transducer means for transmitting pressure from the plug to the pressure transducer means.

23. The pressure measurement device of claim 22 wherein the liquid has a lower viscosity than the plug.

24. The pressure measurement device of claim 22 wherein the plug is a gel-like material.

25. The pressure measurement device of claim 22 wherein the plug is movable with respect to the cavity to compensate for movement of the liquid contained in the lumen and the cavity without building up a pressure differential across the plug.

26. The pressure measurement device of claim 22 wherein a portion of the tube containing the cavity has a smaller wall thickness than a portion of the tube containing the lumen.

27. The pressure measurement device of claim 22 and further comprising a mounting plate through which the distal end of the tube extends.

28. The pressure measurement device of claim 27 wherein the tube has an elbow proximate the mounting plate.

29. The pressure measurement device of claim 22 and further comprising;
a protective sleeve at least partially filled with material which forms the plug and removably mounted on the distal end of the tube.

30. A method of measuring a physiological pressure within a body of an animal, the method comprising:
implanting within the body a pressure measurement device which includes a housing containing a pressure transducer and a transmitter implanted within the body, a pressure transmission catheter connected at a proximal end to the pressure transducer and having a distal end positioned to be exposed to the physiological pressure, the catheter having a lumen extending from the proximal end to the distal end, having a plug of a first flowable material in its distal end and a liquid filling the lumen between the plug and the pressure transducer to transmit the physiological pressure from the plug to the pressure transducer; and
monitoring a signal transmitted by the transmitter as a function of pressure sensed by the pressure transducer.

31. The method of claim 30 wherein the first material is a gel-like material.

32. The method of claim 30 wherein the liquid has a lower viscosity than the first material.

33. The method of claim 30 and further comprising:
attaching a mounting plate, which is connected to the catheter near its distal end, to a body member of the animal.

34. The method of claim 30 and further comprising:
providing a strap around the housing; and
connecting a portion of the strap to the animal.

35. The method of claim 30 wherein the portion of the strap is a connecting flap and wherein the connecting is by sutures.

36. The method of claim 30 and further comprising: soaking the catheter in a saline solution prior to implantng.

37. The method of claim 30 and further comprising: providing a protective sleeve over the distal end of the catheter; and removing the protective sleeve before inserting the distal end into a position where it is exposed to the physiological pressure.

38. The method of claim 30 wherein the plug is movable with respect to the distal end to compensate for movement of the liquid without building up a pressure differential across the plug.

39. The method of claim 30 wherein the physiological pressure is blood presssure and the distal end is positioned in a blood vessel.

40. The method of claim 30 wherein the physiological pressure is intrapleural pressure and the distal end is positioned in a thoracic cavity.

41. The method of claim 30 wherein the physiological pressure is intracranial pressure and the distal end is positioned in a subarachnoid space.

42. A pressure measurement device for measuring a physiological pressure, the device comprising:
pressure transducer means for providing a signal which varies as a function of pressure;
pressure transmitting catheter means for transmitting the physiological pressure to the pressure transducer means, the pressure transmitting catheter means including a hollow flexible tube having a first end for placement at a position at which the physiological pressure is to be measured, a second end in communication with the pressure transducer means, a first material positioned in the tube at the first end, and a liquid which fills the tube and interfaces with the pressure transducer means for transmitting pressure from the first material to the pressure transducer means, wherein the first material is capable of flowing as a viscous fluid and exhibiting a resistance to dissolution, decomposition and mechanical removal from the first end of the tube when subjected to fluid and mechanical forces present when measuring the physiological pressure.

* * * * *

UNITED STATES PATENT AND TRADEMARK OFFICE
CERTIFICATE OF CORRECTION

PATENT NO. : 4,846,191

DATED : July 11, 1989

INVENTOR(S) : Brian P. Brockway

It is certified that error appears in the above-identified patent and that said Letters Patent is hereby corrected as shown below:

Column 11, line 55, delete "then", insert --than--.

Signed and Sealed this

Seventeenth Day of April, 1990

Attest:

HARRY F. MANBECK, JR.

*Attesting Officer*  *Commissioner of Patents and Trademarks*